(12) United States Patent
Ravenscroft

(10) Patent No.: US 7,517,361 B1
(45) Date of Patent: *Apr. 14, 2009

(54) STENT DELIVERY SYSTEM

(75) Inventor: Adrian C. Ravenscroft, Milton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/873,484

(22) Filed: Jun. 12, 1997

Related U.S. Application Data

(63) Continuation of application No. 08/526,968, filed on Sep. 12, 1995, now Pat. No. 5,702,418.

(51) Int. Cl.
*A61F 2/06* (2006.01)

(52) U.S. Cl. ..................................... 623/1.12

(58) Field of Classification Search ...................... 606/1, 606/108, 154, 155, 198, 200; 623/1, 12
See application file for complete search history.

(56) References Cited

U.S. PATENT DOCUMENTS

| | | | | |
|---|---|---|---|---|
| 4,768,507 A | * | 9/1988 | Fischell et al. ............. | 623/1.11 |
| 4,893,623 A | * | 1/1990 | Rosenbluth ................ | 606/192 |
| 5,474,563 A | * | 12/1995 | Myler et al. ................ | 606/108 |
| 5,484,444 A | * | 1/1996 | Braunschweiler et al. .. | 623/1.11 |
| 5,700,269 A | * | 12/1997 | Pinchuk et al. ............. | 606/198 |
| 5,702,418 A | * | 12/1997 | Ravenscroft ............... | 623/1.11 |
| 5,797,952 A | * | 8/1998 | Klein ........................ | 623/1.12 |
| 6,001,123 A | * | 12/1999 | Lau ........................... | 623/1.12 |
| 6,520,983 B1 | * | 2/2003 | Colgan et al. .............. | 623/1.11 |
| 6,576,006 B2 | * | 6/2003 | Limon et al. ............... | 623/1.11 |
| 6,607,551 B1 | * | 8/2003 | Sullivan et al. ............ | 623/1.11 |

* cited by examiner

*Primary Examiner*—Kevin T Truong
(74) *Attorney, Agent, or Firm*—Vidas, Arrett & Steinkraus

(57) ABSTRACT

A stent delivery system a catheter has an axially extending inner core and outer sheath. Axially spaced rings extending from a relatively narrow diameter portion of the inner core proximate the distal end thereof. The rings engage proximal portions of a compacted stent disposed within the sheath and over the core and rings. A proximal handle of the system has a first portion that supports the sheath and a second portion that supports the core for relative displacement of the core and the sheath. Retraction of the sheath relative to the core uncovers the stent engaged by the rings which tends to remain stationary relative to the core so that upon partial retraction of the sheath a distal end of the stent expands to its expanded form. Further retraction of the sheath deploys the stent, retracting the core returns the distal portion of the stent into the sheath.

18 Claims, 3 Drawing Sheets

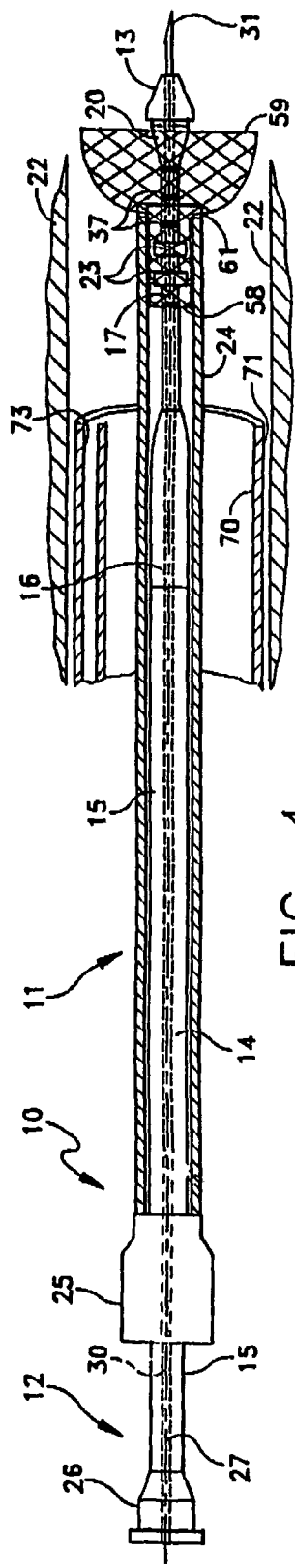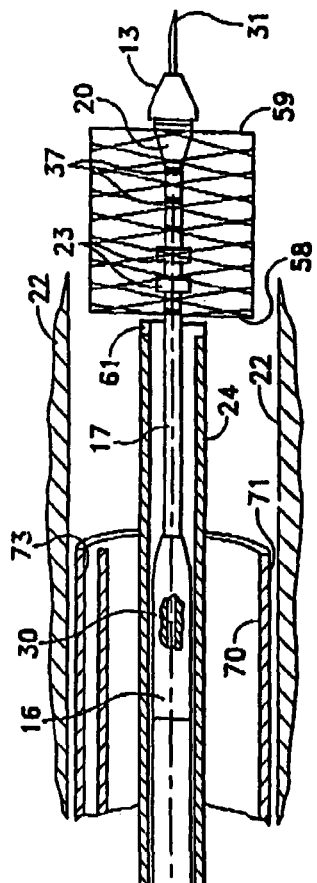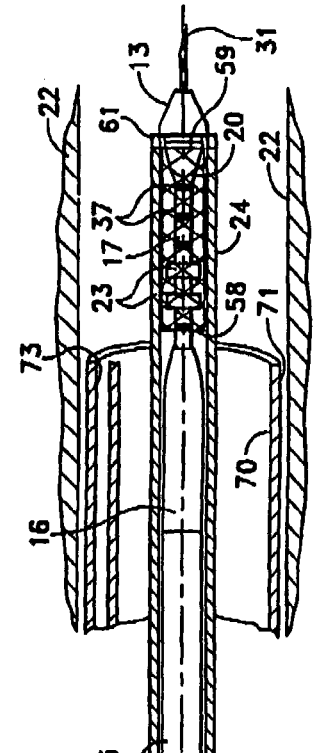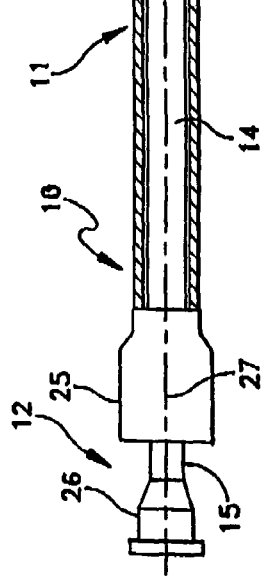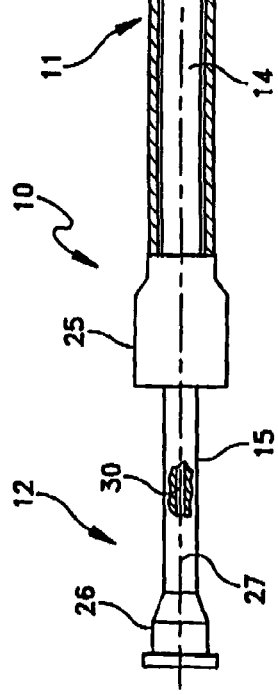

STENT DELIVERY SYSTEM

CROSS REFERENCE TO RELATED APPLICATION

This is a continuation application of our U.S. patent application Ser. No. 08/526,968 filed Sep. 12, 1995 now U.S. Pat. No. 5,702,418 for a Stent Delivery System.

BACKGROUND OF THE INVENTION

1. Field of the Invention

This invention relates to a percutaneous and endoscopic delivery of a stent in a patient's body and more particularly to a stent delivery system including a catheter for the selective deployment of a self-expanding stent.

2. Description of Related Art

Stents are well known endoprostheses. A typical endoprosthetic stent comprises a tubular structure that expands radially from a compact form for transit to an expanded form for implantation. Radial expansion causes the stent to implant into the tissues of a wall of a "vessel" being repaired or bridged to maintain its patency. Such stents may be utilized in body canals, blood vessels, ducts and other body passages, and the term "vessel" is meant to include all such passages.

Stents can be characterized as self-expansive and mechanically expansive. This invention relates to both self-expansive and mechanically expansive stents further characterized by being formed of a single wire or plurality of wires woven together to form a mesh structure which can be located on or in a distal end of a tubular body, such as a medical catheter, in such compact form. A delivery system for such stent comprises a catheter with various associated control mechanisms extending from a distal end to a proximal end. Such a delivery system enables a surgeon to guide the distal end with the compact stent to a selected location in a patient's vessel. The surgeon then operates the control apparatus to release and expand the stent so as to deploy and fix the stent in the selected location. The control apparatus may be integral with the catheter for a mechanically expandable stent or ancillary to the catheter for a self-expansive stent. In either version, the control apparatus releases the stent from the catheter and, in the case of a mechanically expansive stent, expands the stent radially. After the stent has expanded, the surgeon returns the catheter typically to its pre-deployment form, free from the stent, and then removes the catheter from the patient. The expanded stent remains in the vessel in its expanded shape to maintain vessel patency.

Stent delivery systems must generally conform to several important criteria. First, it is critical in most applications to keep the transverse dimension of the delivery system to a minimum, as the distal end of the delivery system typically must be navigated through and along a patient's lumens either in a percantaneous insertion procedure or through the working channel of an endoscope. Second, the delivery system must facilitate the deployment of the stent into contact with the patient's vessel walls once it is located at a selected site. Third, the stent delivery system must easily disengage from the stent after deployment to enable separation of the delivery system from the deployed stent. Fourth, the procedure for removing the delivery system from the body must be straightforward and relatively simple to speed and ease the work of a physician employing the stent delivery system. Fifth, the stent delivery system must be reliable and efficient to reduce trauma and patient risk. Sixth, preferably the delivery system should also enable partial deployment and retraction of the stent to enable the surgeon to recover a stent not properly positioned during deployment thereof.

The prior art stent delivery systems for self-expansive endoprosthetic stents are illustrated by the following United States Letters patent:

U.S. Pat. No. 4,580,568 (1986) Gianturco
U.S. Pat. No. 4,655,771 (1987) Wallsten
U.S. Pat. No. 4,681,110 (1987) Wiktor
U.S. Pat. No. 4,732,152 (1988) Wallsten et al.
U.S. Pat. No. 5,026,377 (1991) Burton et al.

U.S. Pat. No. 4,580,568 to Gianturco discloses a system for delivering a self-expanding stent. The system comprises a tubular sheath positioned with a distal end proximate a selected delivery site. The stent is then compressed and inserted into a proximal end of the sheath. A user inserts a pusher rod into the tubular sheath and urges the stent through the sheath to a position proximate the distal end of the tubular member. The user then retracts the sheath relative to the push rod to release the stent.

U.S. Pat. No. 4,655,771 to Wallsten discloses a delivery system for a stent that includes a catheter that supports a tubular stent in a compact form on its exterior distal end surface. Gripper members proximate the proximal and distal ends of the tubular stent secure to the catheter. A handle at the proximal end of the tubular part of the apparatus enables a user to control the axial movement of the gripper members. That is, axial displacement of the gripper members by the control mechanisms frees the stent from the outer surface of the catheter and enables expansion of the stent.

U.S. Pat. No. 4,681,110 to Wiktor discloses a catheter arrangement in which a tubular member contains a radially expandable liner and a deployment mechanism for deploying the liner. The deployment mechanism includes an internal tube that extends through the outer portion of the tube and engages a proximal end of the liner. Distal displacement of the inner tube relative to the outer tube urges the liner distally of the distal end of the outer tube enables the liner to deploy in its radially expanded form.

U.S. Pat. No. 4,732,152 to Wallsten et al. discloses a device and method for implantation of a prosthetic stent. The stent is maintained in a compact state within the device during transport to a selected location within a patient's vessels and then is released to expand and fix in a patient's vessel.

The following United States Letters Patent illustrate prior art stent delivery systems for mechanically expansive stents:

U.S. Pat. No. 4,553,545 (1985) Maass et al.
U.S. Pat. No. 4,733,665 (1988) Palmaz
U.S. Pat. No. 4,907,336 (1990) Gianturco
U.S. Pat. No. 4,950,227 (1990) Savin et al.

U.S. Pat. No. 4,553,545 to Maass et al. discloses a coil spring stent and an instrument for transporting the stent in a compact form and then deploying the stent in an expanded form within a patient's body. A tubular body carried on the distal end of a catheter underlies and supports the stent. Proximal and distal ends of the stent are clamped between the ends of the tubular body and enlarged first and second end sections of the catheter. The end sections connect by first and second portions of a coaxial cable to a knob member at a proximal end of the instrument. A second knob member at the proximal end connects with the tubular body so that relative rotation of the knobs in a first sense urges rotation of the tubular body relative to the end section to urge radial expansion of the stent thereby. Opposite rotation of the knobs tend to contract the stent. Successive opposed relative axial displacement of the knobs successively widens the space between the first and second end sections respectively and the tubular body to thereby release the stent from the tubular member.

U.S. Pat. No. 4,733,665 to Palmaz and U.S. Pat. No. 4,907,336 to Gianturco disclose a stent delivery system with a mesh and wire stent respectively, mounted on an expandable balloon at a distal end of the catheter. A surgeon positions the distal end of the catheter in a patient's vessel and expands the balloon and stent into contact with the vessel wall. Then the surgeon deflates the balloon and removes the catheter.

In U.S. Pat. No. 4,950,227 to Savin et al. a stent is placed at a distal end of a catheter surrounding an expandable balloon. Proximal and distal ends of the stent underlie flaps on the outer surface of the catheter. Expansion of the balloon releases the stent from the flaps and expands the stent into its operative expanded form.

In U.S. Pat. No. 5,026,377 to Burton et al. an outer sheath overlies a stent carried in a compact form at the extreme distal end of the catheter. An elongated gripping member supported by an inner core frictionally grips the stent in its compact form. Manipulation of a proximal handle member selectively retracts the sheath to expose the self-expanding stent and enables deployment at the select location. At an intermediate position a physician can selectively retract the inner core to retract the stent within the outer sheath.

Burton et al. do provide apparatus that enables a surgeon to retract a stent after displacement has begun. However, Burton et al. do not provide any indication that the stent has deployed beyond a point at which retraction is no longer possible. That is, Burton et al. fail to disclose apparatus enabling a surgeon to determine when the axial forces necessary to reduce the expanded portion of the stent have exceeded the frictional bond between the stent and a gripping surface that retains the stent on the catheter. Furthermore, in the prior art, such as that disclosed by Burton et al., the stent in its compact form is closely proximate both a core and an outer sheath. The inner stent surface bears on the core and the outer stent surface bears on the inner sheath surface to thereby form a frictional engagement therebetween. This also reduces the overall flexibility of the distal end of the stent delivery system. Maneuvering a distal end of reduced flexibility through the tortuous paths often encountered in a patient's vessels can increase patient trauma and can, in some cases, make this treatment modality impracticable. Thus, a surgeon frequently faces the decision of risking additional trauma to the patient or adopting another procedure for treating the patient. Thus, none of these prior art delivery systems and methods enable the delivery of a stent to a selected location of patient's body and facilitate the retraction of a partially deployed stent, that provides reasonable flexibility of the distal end for positioning the stent at the selected location and that provides to a physician a defined zone of retractability of the stent.

SUMMARY

Therefore, it is an object of this invention to provide a method and system for either percantaneous or endoscopic delivery of a stent at a selected location in a vessel of a patient.

It is another object of this invention to provide a stent delivery system with a flexible distal end adapted for passage through the vessels of a patient and with the capability of selective deployment and retraction of the stent.

It is still another object of this invention to provide a stent delivery system with capability of selective deployment and retraction of the stent characterized by a flexible distal end for use in percantaneous and endoscopic procedures and adapted for passage through tortuous paths defined by the vessels of a patient.

It is yet another object of this invention to provide a method and system for delivery of a stent which reduces the steps and time necessary to deliver a stent to a selected location of a vessel in a patient.

It is yet still another object of this invention to provide a method and system for delivery of a stent which enables a user to ascertain whether the stent is retractable.

It is a further object of this invention to provide a method and system for delivery of a stent which is relatively simple and inexpensive to produce and use.

In accordance with one aspect of this invention a delivery system for positioning a stent in a patient's vessel includes a catheter for positioning the stent at a predetermined position in the patient's body. The catheter includes a sheath normally overlying the stent in its compact form and an inner core normally underlying the stent in its compact transport form. Two spaced rings extend radially from the inner core and engage the stent in its compact form to enable deployment of the stent by distal displacement thereof relative to the sheath and retraction of the stent within the sheath by proximal displacement thereof relative to the sheath.

According to another aspect of this invention a delivery system includes a distal end having a flexible sheath and a flexible core at a distal end of the system for overlying and underlying, respectively, a self-expansible stent positionable in a compact form. The stent is supported on at least two spaced rings secured to the core. Retracting the sheath relative to the core deploys the stent; retraction of the core relative to the sheath prior to full deployment of the stent retracts the stent relative to the sheath.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view in partial cross-section illustrating an embodiment of a stent delivery system according to this invention;

FIG. 4 is a plan view of the embodiment of FIG. 1 with the stent in a partially deployed position;

FIG. 5 is a plan view of the embodiment of FIG. 1 with the stent in a fully deployed position;

DESCRIPTION OF ILLUSTRATIVE EMBODIMENTS

Figure 3:
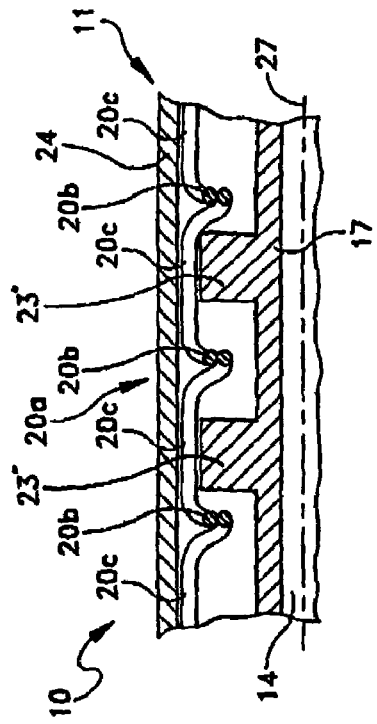
FIG. 3 is a sectional view taken along the line 3-3 in FIG. 2.

A stent delivery system 10 according to this invention as depicted in FIG. 1 includes a elongated catheter 11 defined between a proximal handle 12 and a distal end tip 13. An axially extending plastic core 14 supports the distal end tip 13. The core 14 includes a relatively stiff portion 15 extending distally from the handle 12. A flexible thick portion 16 extends distally from the stiff portion 15. A flexible thin distal portion 17 extends between the portion 16 and the distal end tip 13. The flexible thin portion 17 underlies a mesh stent 20 supported in a compacted form within the catheter 11 proximate the distal end tip 13 for deployment from the catheter 11 in an expanded form within a patient's vessel 22.

First and second closely, but axially spaced rings 23 attach to the thin portion 17 and engage the stent 20. A slippery outer sheath 24, preferably formed of a radially flexible axially stiff material such as Teflon® or other like material, overlies the stent 20 and extends proximally to a first handle portion 25. The stiff portion 15 of the core 14 secures to a second handle portion 26. The handle portions 25 and 26 are displaceable along the axis 27 relative to each other thereby to enable selective deployment and retraction of the stent 20.

In the embodiment of FIG. 1, the stiff portion 15 of the core 14, which extends a substantial length of the catheter 11, is preferably formed of a plastic material such as PEBAX® or an elongated coiled spring formed of plastic or metal such as Nitinol® which provides limited flexibility so the catheter 11 can readily be pushed from the handle 12 through the patient's vessel with little risk of kinking. The core portions 16 and 17 are relatively flexible radially.

The presence of the stent 20 on the axially spaced rings 22 does not significantly retard the overall flexibility of the extreme distal end of the catheter 11, because the rings 23 which support the stent 20 are substantially spaced from the distal end tip 13. That is, the distal portion of the stent 20 floats in a radial sense over the core 17. Thus upon application of a radially directed force to the sheath 24 proximate the distal end tip 13, the stent 20 tends to radially displace within the sheath 24 thereat. This feature eases the surgeon's task in navigating the catheter 11 through severely tortuous paths often associated with both endoscopic and percantaneous procedures. Thus, employment of this invention reduces the steps and time necessary for delivery of a stent to a delivery site.

Once the system 10 is properly inserted, the distal end tip 13 will be positioned at a selected location in a patient's vessel 22 for deployment of the stent 20. This can be accomplished by various means, particularly Applicant prefers providing markers such as radio opaque rings or indicia 37 on the core 17 proximate the distal end tip 15 to properly locate the system 10. Then a surgeon will operate the handle 12 to deploy the stent 20.

Figure 2:
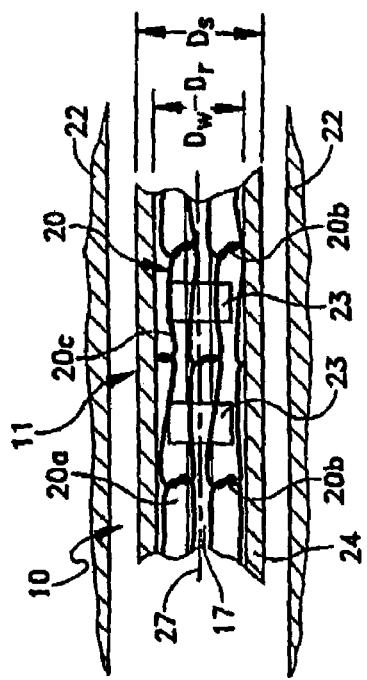
FIG. 2 is an enlarged view of a distal end of the embodiment of FIG. 1.

As best seen in FIGS. 2 and 3, the stent 20 preferably comprises a plurality of interlocking loops 20A having spaced overlapping portions 20B and single wire portions 20C intermediate thereof. The individual wires preferably have a diameter "$D_w$", the rings 23 have an outer diameter "$D_r$", and the sheath 24 has an inner diameter "$D_s$", wherein:

$$4D_w + D_r > D_s > 2D_w + D_p \quad (1)$$

Likewise the stent 20 when in its compact form has an outer diameter approximately "$D_s$" and maximum inner diameter ($ID_{max}$) and minimum inner diameter ($ID_{min}$) where:

$$ID_{max} \approx D_s - 2D_w \quad (2)$$

and $$ID_{min} \approx D_s - 4D_w \quad (3)$$

The outer diameter "$D_r$" of the rings 23 therefore is preferably between the maximum and minimum inner diameters of the stent 20 in its compact form. Thus, as depicted in FIG. 1A, the stent 20 is positioned within the sheath 24 with the single wire portions 20C overlying the rings 23 and the overlapping portions 20B disposed between adjacent rings 23.

Thus, upon distal displacement of the rings 23 distal faces of the rings 23 engage proximal surfaces of distally adjacent overlapping portions 20B to urge corresponding distal displacement of the stent 20. Likewise upon proximal displacement of the rings 23 proximal faces of the rings 23 engage distal surfaces of proximally adjacent overlapping portions 20B to urge corresponding proximal displacement of the stent 20. As will now be appreciated the positive engagement between the stent 20 and the rings 23 due to the interspersed portions of the stent having large and small inner diameters, $ID_{max}$ and $ID_{min}$, enable the selective and relatively sure control of the surgeon in deploying and retracting the stent 20.

In the embodiment of this invention illustrated by FIG. 1, the surgeon preferably grasps the handle portion 25 and the handle portion 26 with two hands, holds the handle portion 26 steady and retracts the handle portion 25. This retracts the sheath 24 relative to the core 14. When the surgeon partially retracts the sheath to a position as shown in FIG. 4, the distal portion of the stent 20 beyond the sheath expands. The surgeon can uses fluoroscopic or endoscopic viewing techniques and apparatus to determine whether the stent 20 is appropriately positioned. If the stent 20 is not properly positioned the surgeon displaces the handle portion 26 proximally to retract the core 14, attached rings 23 and the stent 20 fully within the sheath 24 so that the stent 20 and delivery system returns to the condition as depicted in FIG. 1. The distal end can then be maneuvered to a desired location or into a desired orientation and the process repeated. Once the surgeon is satisfied with the location and orientation of the partially deployed stent 20, the surgeon merely fully retracts the handle 25 to fully deploy the stent 20 as depicted in FIG. 5.

Those skilled in the art will now recognize that the ability to retract a partially deployed stent enables a surgeon to ascertain whether the stent 20 is properly positioned fluoroscopically and/or visually through an endoscope before fully deploying the stent 20. This can be important to both surgeon and patient as improper positioning can increase the trauma and risk to a patient and curtail the efficiency of the treatment. As is known, manipulation of handles at the proximal end of a catheter to deploy a stent often affects the site of deployment of the stent as the distal end of the catheter can be unintentionally translated by such manipulation. Likewise other factors, some of which are only apparent upon deploying the stent can render a location initially thought to be inappropriate. For these reasons, the embodiment of FIG. 1 includes the indicia 37 thereon, so that a surgeon using a fluoroscope or viewing channel of an endoscope can ascertain the extent of deployment of the stent 20, as more fully discussed below.

Figure 6:
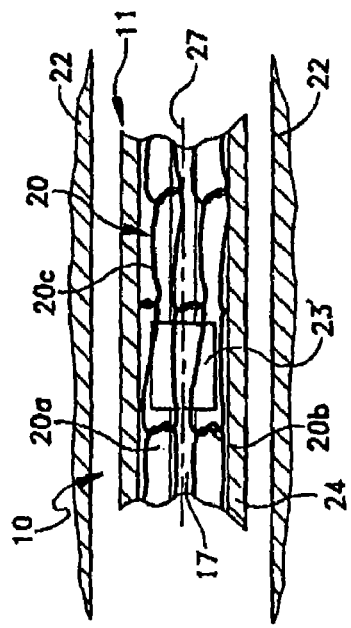
FIG. 6 is an enlarged plan view similar to FIG. 1A of another embodiment of this invention.

FIG. 6 depicts another embodiment of this invention. A single ring 23' mounts to the catheter. It has a slightly longer axial extension than each ring 23, but less than the axial distance between the interlocking loops 20A. The ring 23' has an outer diameter ($D_r'$), that satisfies the conditions:

$$D_r' + 4D_w > D_s > D_r' + 2D_w \quad (4)$$

The operation and use of this embodiment is similarly identical to the embodiment of FIG. 1.

Figure 7:
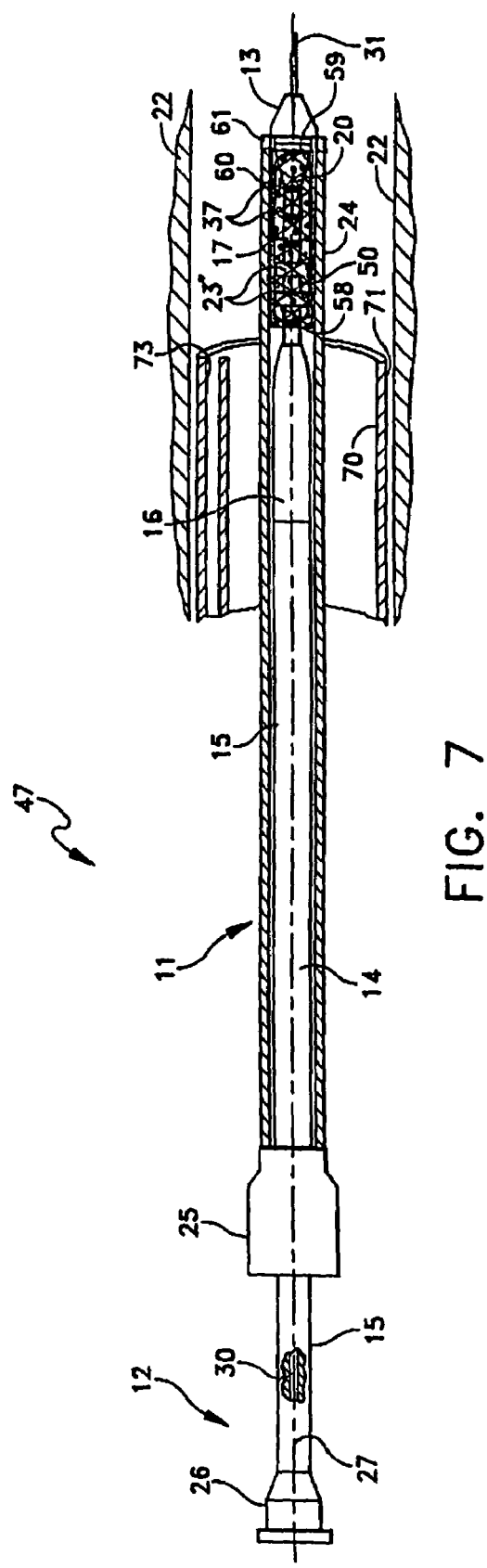
FIG. 7 is a plan view similar to FIG. 1 of yet another embodiment of this invention particularly useful in deploying a non-self-expanding stent.

Referring now to FIG. 7, another delivery system 47 according to this invention includes the annular rings 23" that support a stent 50 in a compact form. The stent 50, rather than being a self-expanding stent, is formed with a known material defining the mechanically expansible mesh that locks in an expanded form. The annular rings 23" engage the stent 50 in its compact form to enable retraction of the stent 50 by retraction of the handle portion 26 and to prevent retraction of the stent 50 when the sheath 24 is retracted by operation of the handle 25. In this embodiment, a balloon lumen (not shown) connects to an expansible balloon 60 that underlies the stent 50 between proximal to distal ends 58 and 59. The balloon 60 also lies between the rings 23 and the stent 50. If the sheath 24 is partially retracted to a position similar to that of FIG. 2, inflating the balloon 60 expands only the exposed portion of the balloon 60 and the coextensive portion of the stent 50 that lies distally of the sheath 24.

If repositioning of the stent is required, the surgeon deflates the balloon 60 and retracts the core portion 17 to thereby contract the stent 50 to enable repositioning of the distal end of the system 47. In this embodiment an extreme distal end of the sheath 24 preferably includes an integral metal or hard plastic ring 61 to assist in the compression of the stent 50 upon retraction thereof from is partially deployed condition. Once the stent 50 is partially deployed in a satisfactory position, the surgeon fully retracts the sheath 24 and fully inflate the balloon 60 to fully deploy the stent 50 thereat.

As previously indicated, the particular structures of the stent delivery systems according to this invention are suited for use in procedures using either percantaneous or endoscopic insertion techniques. In an endoscopic insertion technique the surgeon inserts the catheter 11 through the working channel 70 of an endoscopic device 71 (see FIG. 5). In either technique a central lumen such as lumen 30 in FIG. 4, can extend through the catheter 11 receive a guidewire 31. With the central lumen 30, the surgeon can first position the guidewire 31 in the patient and then slide the catheter 11 over the guidewire 31 to position the catheter 11 within the patient's vessels with relative ease.

In accordance with another aspect of this invention, the distal end tip 13 can be formed of a radiopaque material or provided with a radiopaque marker to improve fluoroscopic observation of the distal end of the systems 10 and 47 of FIGS. 1 and 7. The core portion 17 and the extreme distal end 61 of the sheath 24 can also be provided with indicia 37 to indicate extension of the core 17 relative to the sheath. The indicia 37 and 61 will generally be radiopaque indicia although in devices according to this invention used with an endoscope 71 having a viewing channel 73, the indicia 37 and 61 may be of a type only visually perceived (e.g. colored rings). Preferably the indicia 37 is arranged in a selected number; concentration and/or color to indicate when the degree of deployment has reached a state where further distal displacement of the rings will render subsequent retraction of the stent impossible. Thus, a surgeon upon observing the selected indicia 37 that the commitment to deploy or retract must be made.

Thus, the stent delivery system of this invention enables a surgeon to position a compacted stent at a selected location and partially deploy the stent, then either fully deploy the stent or return the stent to its compacted form. A surgeon after partially deploying a stent can, upon observing a problem such as incorrect positioning or the like, retract the stent within the sheath 24 and then reposition the distal end 13 at a selected location and commence deployment of the stent. The use of one or more of the rings 23, 23' or 23" also tends to improve the radial flexibility of the distal end of the stent delivery systems according to this invention as compared with such prior art systems. As should now be understood, the rings 23, 23' and 23" disclosed herein are structures that interlock with the stent when in its compact form. This interlocking provides the improved control of the stent in deploying and retracting the stent relative to the catheter.

This invention has been disclosed in terms of certain embodiments. It will be apparent that many modifications can be made to the disclosed apparatus without departing from the invention. By way of example, additional rings to engage the stent may be employed, the rings or rings used may included slots for receiving portions of the stent overlying the rings, and, in fact, a ring can be formed or defined by a plurality of protuberances or fingers that extend from a core or similar structure to engage and interlock with portions of the stent with the minimum inner diameter. Therefore, it is the intent of the appended claims to cover all such variations and modifications as come within the true spirit and scope of this invention.

What is claimed as new and desired to be secured by Letters Patent of the United States is:

1. A stent delivery system for transporting and deploying an expansible stent, said stent delivery system comprising:
    A) delivery means for positioning the stent at a selected position in the patient's body, said delivery means including a sheath normally overlying the stent in its compact transport form, the stent having an inner surface, the sheath having a ring, the ring forming a distal end of the sheath, the ring assisting in the compression of the stent to the compact transport form from a partially deployed form, and an inner core normally underlying the stent in its compact transport form, and
    B) deployment means for selectively deploying and retracting the stent relative to said sheath, said deployment means including at least two rings attached to and extending from said inner core and engaging the inner surface of the stent in its compact condition.

2. A stent delivery system as recited in claim 1 wherein an outer diameter of at least one of said at least two rings is greater than a minimum inner diameter ($ID_{min}$), of portions of the stent in its compacted form.

3. A stent delivery system as recited in claim 2 wherein at least one of said at least two rings engage the stent proximate a proximal end of the stent in its compact transport form.

4. A stent delivery system as recited in claim 3 wherein said delivery means further includes a handle disposed at a proximal end of said sheath and said inner core, said handle having a first actuator means for proximally retracting said sheath relative to said inner core and a second actuator means for distally displacing said inner core relative to said sheath, such that selective manipulation of said first and second actuator means enables selective deployment of the stent in an expanded form outside of said sheath and retraction of the stent within said sheath from a partially deployed state.

5. A stent delivery system as recited in claim 1 wherein said delivery means is adapted for use in a working channel of an endoscopic device of the type having a viewing channel, said delivery means including visible indicia proximate its distal end visible through the viewing channel of the endoscopic device indicating the extent of deployment of the stent.

6. A stent delivery system as recited in claim 5 wherein said delivery means further includes a handle disposed at a proximal end of said sheath and said inner core, said handle having a first actuator means for proximally retracting said sheath relative to said inner core and a second actuator means for distally displacing said inner core relative to said sheath, such that manipulation of said first and second actuator means enables selective deployment of the stent in an expanded form outside of said sheath and retraction of the stent in the compact form within said sheath.

7. A stent delivery system as recited in claim 1, the at least two rings comprising a first ring and a second ring, wherein the second ring is axially spaced from said first ring, said first and second rings engaging the stent proximate a proximal end of the stent in its compact form.

8. A stent delivery system as recited in claim 7 wherein said delivery means further includes a handle disposed at a proximal end of said sheath and said inner core, said handle having a first actuator means for proximally retracting said sheath relative to said inner core and a second actuator means for distally displacing said inner core relative to said sheath, such that manipulation of said first and second actuator means enables selective deployment of the stent in an expanded form outside of said sheath and retraction of the stent within said sheath from a partially deployed condition in the compact form.

9. A stent delivery system as recited in claim 8 wherein said delivery means is adapted for use in a working channel of an endoscopic device of the type having a viewing channel, said delivery means including visible indicia proximate its distal end visible through the viewing channel of the endoscopic device indicating the extent of deployment of the stent.

10. A stent delivery system as recited in claim 1 wherein said delivery means is adapted for use in a working channel of an endoscopic device of the type having a viewing channel, said delivery means including visible indicia proximate its distal end visible through the viewing channel of the endoscopic device indicating the extent of deployment of the stent.

11. An elongated, tubular stent delivery system for transporting a stent in a compact form within a patient's body for selective deployment of the stent in an expanded form within a patient's vessel comprising a distal end region including a sheath and a flexible core at the distal end region for overlying and underlying, respectively, a stent carried at the distal end region of the delivery system in the compact form, the stent having an inner surface, and a proximal end region including a first handle portion connected to the sheath and a second handle portion connected to the core to enable relative axial displacement of the sheath and the core, the improvement comprising at least two rings engaged to and extending from the core to engage the inner surface of the stent disposed in the compact form within said sheath such that upon the displacement of the sheath relative to the core the stent moves relative to the sheath, the sheath comprising a ring, the ring forming a distal end of the sheath, the ring assisting in the compression of the stent to the compact form from a partially deployed form.

12. A tubular stent delivery system as recited in claim 11 wherein each of said at least two rings has an outer diameter $D_r$, such that $D_r > ID_{min}$, a minimum inner diameter of portions of the stent in its compacted form.

13. A tubular stent delivery system as recited in claim 12 wherein at least one of said at least two rings engages the stent proximate a proximal end of the stent in its compact form.

14. A tubular stent delivery system as recited in claim 13 wherein said stent has portions with an inner diameter $ID_{max}$ disposed between portions of the stent having its minimum inner diameter where $ID_{min} < D_r < ID_{max}$ and each of said at least two rings is disposed intermediate the minimum inner diameter portions.

15. A tubular stent delivery system as recited in claim 14 wherein said delivery system is adapted for use in a working channel of an endoscopic device of the type having a viewing channel and the distal end of the stent having indicia proximate the distal end of the core, said indicia being of the type visible through the viewing channel of an endoscopic device and indicating the extent of deployment of the stent.

16. A tubular stent delivery system as recited in claim 11, the at least two rings comprising a first ring and a second ring, wherein the second ring is secured to the core proximate to and axially spaced from the first ring, wherein said first and second rings are proximally spaced from a distal end of the stent in its compacted delivery state.

17. A method for delivering and selectively deploying a stent comprising the steps of:
A) inserting an axially extending catheter within the body of a patient, the catheter having an exterior sheath, the exterior sheath having a ring, the ring forming a distal end of the exterior sheath, with a stent in a compact form proximate a distal end of the catheter, the stent underlying the sheath and overlying at least two rings, the ring of the exterior sheath assisting in the compression of the stent to the compact form from a partially deployed form,
B) urging the distal end of the catheter through the patients body to position the distal end at a selected location, and
C) selectively displacing the at least two rings relative to the sheath to urge the displacement of said stent relative to the sheath to enable selective extension and retraction of the stent relative to a distal end of the sheath.

18. A method for delivering and selectively deploying a stent as recited in claim 17 wherein the stent is self-expansive and said step of selectively displacing the at least two rings relative to the sheath to urge displacement of said stent relative to the sheath to enable selective extension and retraction of the stent relative to a distal end of the sheath includes engaging the inner surface of the stent between portions of the stent having a minimum inner diameter.

* * * * *